United States Patent
Michler et al.

(10) Patent No.: US 10,426,488 B2
(45) Date of Patent: *Oct. 1, 2019

(54) EXCLUSION OF THE LEFT ATRIAL APPENDAGE

(71) Applicants: Robert E. Michler, Riverside, CT (US); Albert N Santilli, Pepper Pike, OH (US)

(72) Inventors: Robert E. Michler, Riverside, CT (US); Albert N Santilli, Pepper Pike, OH (US)

(*) Notice: Subject to any disclaimer, the term of this patent is extended or adjusted under 35 U.S.C. 154(b) by 303 days.

This patent is subject to a terminal disclaimer.

(21) Appl. No.: 15/339,027

(22) Filed: Oct. 31, 2016

(65) Prior Publication Data

US 2017/0065280 A1 Mar. 9, 2017

Related U.S. Application Data

(63) Continuation of application No. 11/315,799, filed on Dec. 22, 2005, now Pat. No. 9,486,225.

(51) Int. Cl.
*A61B 17/122* (2006.01)
*A61B 17/00* (2006.01)

(52) U.S. Cl.
CPC ...... *A61B 17/1227* (2013.01); *A61B 17/0057* (2013.01); *A61B 2017/00243* (2013.01); *A61B 2017/00584* (2013.01); *A61B 2017/00632* (2013.01)

(58) Field of Classification Search
CPC . A61B 17/083; A61B 17/122; A61B 17/1227; A61B 17/0057; A61B 17/1285; A61B 17/10; A61B 17/128; A61B 2017/2837; A61B 17/0487; A61B 17/08; Y10S 227/902
See application file for complete search history.

(56) References Cited

U.S. PATENT DOCUMENTS

| | | | | |
|---|---|---|---|---|
| 5,354,306 A | * | 10/1994 | Garvey, III | A61B 17/122 24/563 |
| 9,480,480 B2 | * | 11/2016 | Santilli | A61B 17/1227 |
| 9,486,225 B2 | * | 11/2016 | Michler | A61B 17/1227 |
| 2005/0277959 A1 | * | 12/2005 | Cosgrove | A61B 17/12 606/151 |

* cited by examiner

*Primary Examiner* — Gregory A Anderson
(74) *Attorney, Agent, or Firm* — Wayne D. Porter, Jr.

(57) ABSTRACT

A device for excluding the left atrial appendage (LAA) includes first and second members, each with first and second ends. The second ends are connected by a hinge. The first ends interlock to close the device about the LAA. The members are shaped such that they can exclude the LAA without causing the development of necrotic tissue. If desired, a flexible cover can be provided and the first and second members can be disposed within the cover. If such a cover is used, it will contact the LAA in order to cushion the contact between the members and the LAA and minimize the tendency of the LAA to bleed. The invention also includes methods for using the device to exclude the LAA.

20 Claims, 4 Drawing Sheets

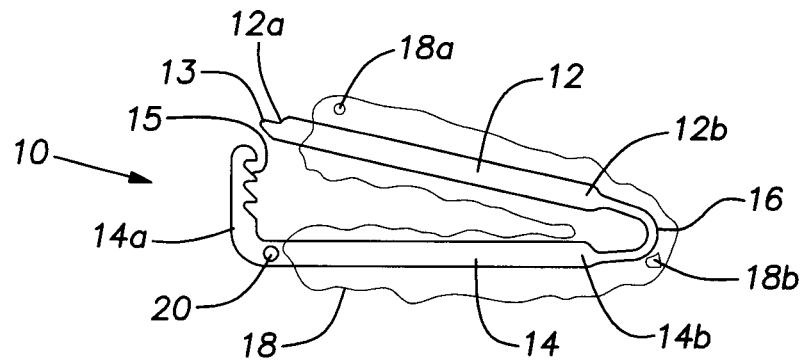
Fig. 2
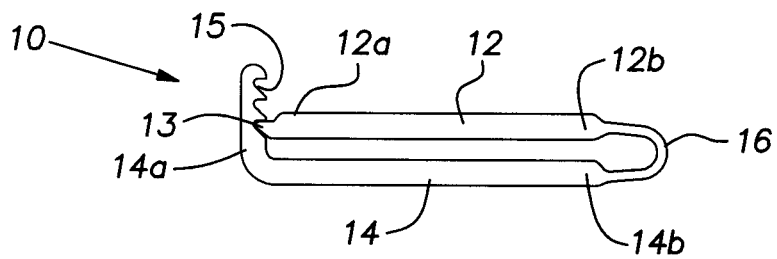
Fig. 3
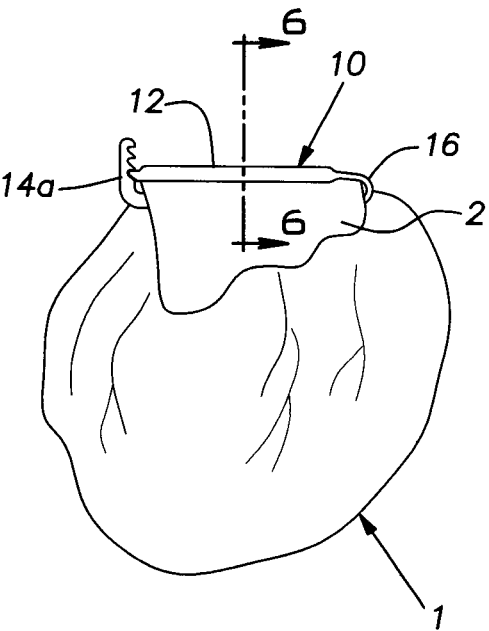
Fig. 4
Fig. 5

EXCLUSION OF THE LEFT ATRIAL APPENDAGE

The present application is a continuation of application Ser. No. 11/315,799, filed Dec. 22, 2005 by Robert E. Michler and Albert N. Santilli, entitled Exclusion of the Left Atrial Appendage ("the LAA patent"), the disclosure of which is incorporated herein by reference for all purposes.

BACKGROUND OF THE INVENTION

1. Field of the Invention

The invention relates to techniques for exclusion of the left atrial appendage and, more particularly, to a device that can be applied to the exterior of the left atrial appendage in order to prevent the formation of embolisms associated with atrial fibrillation.

2. Description of the Prior Art

Embolic stroke is a major cause of disability and death. The most common cause of embolic stroke emanating from the heart is thrombus formation due to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in large part, to the fear of a stroke, and the pharmaceutical regimen necessary to reduce that risk.

For patients who have atrial fibrillation and develop atrial thrombus therefrom, the clot normally occurs in the left atrial appendage (LAA) of the heart. The LAA is a cavity that is connected to the lateral wall of the left atrium between the mitral valve and the root of the left pulmonary vein. The LAA normally contracts with the rest of the left atrium during a normal heart cycle, thus keeping blood from becoming stagnant therein. However, the LAA, like the rest of the left atrium, does not contract in patients experiencing atrial fibrillation due to the discoordinate electrical signals associated with atrial fibrillation. As a result, thrombus formation is predisposed to form in the stagnant blood within the LAA. Of the patients with atrial thrombus, a large majority have the atrial thrombus located within the LAA. The foregoing suggests that the elimination or containment of the thrombus formed within the LAA of patients with atrial fibrillation would significantly reduce the incidence of stroke in those patients.

Pharmacological therapies for stroke prevention such as oral or systemic administration of blood thinning agents, such as warfarin, coumadin or the like have been inadequate due to serious side effects of the medications (e.g. an increased risk of bleeding) and lack of patient compliance in taking the medication.

As an alternative to drug therapy, invasive surgical procedures for closing or altering the LAA have been proposed. For example, U.S. Pat. No. 6,652,555 discloses a barrier device in the form of a membrane for covering the ostium of the LAA to prevent blood clots in the LAA from escaping and entering the blood stream. Published U.S. Patent Application No. 2005/0004652 discloses an occlusion device for inhibiting compression of the LAA in which tissue ingrowth onto the occlusion member is provided. Both of these devices are extremely invasive in that the LAA must be opened (usually during the course of open heart surgery) and a foreign device implanted therein. The implanting process itself is time consuming to perform and increases the risk of hemorrhage and infection.

Another approach has been to attempt to close the LAA by means of an externally applied device or instrument. For example, U.S. Pat. No. 6,488,689 discloses that closure of the LAA can be accomplished by a loop of material, such as a suture, wire, tape, mesh, or the like, which can be applied over the LAA and cinched in place to close the LAA. The '689 patent also discloses that closure can be accomplished by stapling, clipping, fusing, gluing, clamping, riveting, or the like. Published U.S. Patent Application Nos. 2005/0149068 and 2005/0149069 disclose several types of clamps that can be fitted about the LAA externally and the compressed against the LAA.

Unfortunately, although externally applied devices and techniques appear to offer a relatively simple and effective approach to the problem of excluding the LAA, certain problems have not been addressed. A significant problem that remains is that of tissue necrosis. If the compressive force that is applied to the LAA is too great, or if compression is localized is some areas and not others, the device either could cause undesired cell destruction or it could fail to perform its exclusion function properly. Another problem that remains is that of unintended hemorrhaging due to punctures formed being in the surface of the LAA. This is an important issue due to the tendency of the LAA to bleed easily.

Desirably, an externally applied exclusion device for the LAA would be available that would be easy to apply. Any such device preferably would apply the proper amount of compressive force to exclude the LAA while avoiding any stress concentrations that would lead to undesired tissue necrosis. Moreover, any such device hopefully would avoid punctures that would lead to difficult-to-control bleeding.

SUMMARY OF THE INVENTION

In response to the foregoing concerns, the present invention provides a new and improved technique for excluding the LAA. The invention includes a device having a first member having first and second ends adapted to extend from one side of the LAA to the other and to contact the LAA on a selected side thereof adjacent the heart and a second member having first and second ends adapted to extend from one side of the LAA to the other and to contact the LAA on the other side thereof adjacent the heart. The first and second members in use are disposed generally parallel with each other and are disposed sufficiently close to each other to compress the LAA between them without causing the development of necrotic tissue. Those portions of the first and second members that contact the LAA are configured to minimize stress concentrations in the LAA.

Preferably, those portions of the first and second members that come into contact with the LAA are rounded. It also is possible for the first and second members, in cross-section, to be rectangular with rounded ends, the longer dimension of the rectangle adapted to contact the LAA. The first and second members may be straight, or they can have a non-straight configuration such as arc-shaped when viewed from above. In the preferred embodiment, a hinge connects the second ends of the first and second members, the hinge comprising an integral extension of the second ends of the first and second members. The preferred embodiment also provides that the first ends of the first and second members interlock with each other to maintain the first and second members in a fixed position relative to each other.

It is possible to provide a flexible cover for the first and second members. The cover can be made of a number of materials that are biocompatible with the LAA, but a flexible covering in the form of a mesh made of polyester fabric is preferred. Such a flexible cover will tend to cushion the contact between the LAA and the device and will assist in preventing undesired bleeding.

The invention also includes a method for excluding the left atrial appendage (LAA), comprising the step of providing a first, elongate member having first and second ends, the first member having a cross-section that will minimize stress concentrations in the LAA, the first member being long enough to extend from one side of the LAA to the other. The method also includes the step of providing a second, elongate member having first and second ends, the second member having a cross-section that will minimize stress concentrations in the LAA, the second member being long enough to extend from one side of the LAA to the other. The method provides for disposing the first and second members on either side of the LAA adjacent the heart with the first and second members generally parallel with each other and for moving the first and second members sufficiently close to each other to compress the LAA between the first and second members without causing the development of necrotic tissue. The method also calls for maintaining the first and second members in a compressed position relative to the LAA.

Further embodiments of the method according to the invention include the step of providing a flexible container for the first and second members, the container being long enough to receive both the first and second members, the container being made of a material that is biocompatible with the LAA, and placing the first and second members in the container prior to the step of disposing the first and second members on either side of the LAA adjacent the heart with the longitudinal axes of the first and second members generally parallel with each other. If desired, the method can include the step of suturing the flexible container to the LAA.

By using the present invention, a surgeon can quickly and easily exclude the LAA. The device according to the invention applies the proper amount of compressive force to exclude the LAA while avoiding stress concentrations that would lead to undesired tissue necrosis. Moreover, the device will avoid punctures that would lead to difficult-to-control bleeding. The foregoing and other features and advantages of the invention will be apparent from a review of the following description of the invention, taken together with the attached drawings,

BRIEF DESCRIPTION OF THE DRAWINGS

FIG. 2 is a side elevation view of an exclusion device in accordance with one embodiment of the present invention, the embodiment shown being in an open position and having a flexible cover coupled thereto;

FIG. 3 is a view of the exclusion device of FIG. 2 with the cover removed and the device in a closed position;

FIG. 4 is a perspective view of the device of FIG. 2 with the cover removed and the device in an open position;

FIG. 5 illustrates the device of FIGS. 2-3 as used on a heart to exclude the LAA;

DESCRIPTION OF THE PREFERRED EMBODIMENTS

Figure 1:
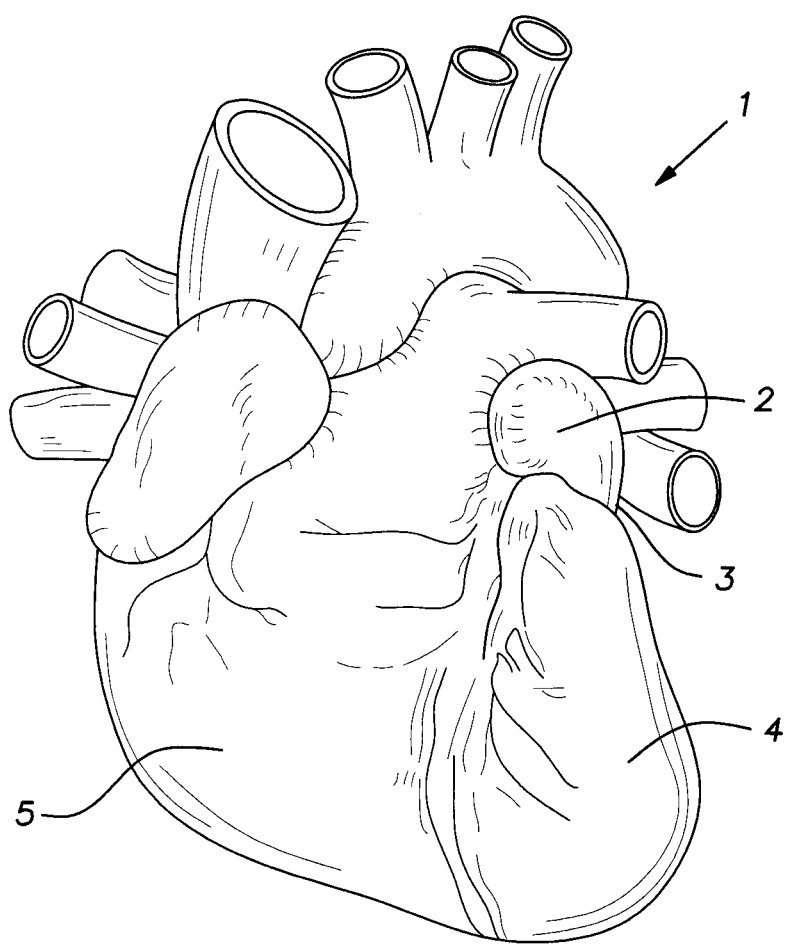
FIG. 1 is a perspective view of a heart illustrating the location of the LAA relative to other structures of the heart.

FIG. 1 shows an anterior view of a heart 1. The heart 1 has a right ventricle 5, a left ventricle 4, and a left atrial appendage (LAA) 2. The methods and devices of the present invention involve the placement of an exclusion device over a base region 3 of the LAA 2 to help prevent thrombi or blot clots inside of the LAA 2 from escaping the LAA 2. It is expected that the elimination or containment of thrombi formed within the LAA of patients with atrial fibrillation will significantly reduce the incidence of stroke in these patients.

Referring to FIGS. 2-7, a device for excluding the LAA 2 according to the invention is indicated generally by the reference numeral 10. The exclusion device 10 includes a first member 12 and a second member 14. The first member 12 has a first end 12a and a second end 12b that lie in a first plane. The second member 14 also has a first end 14a and a second end 14b that lie in a first plane. The first member 12 and second member 14 are adapted to extend from one side of the LAA 2 to the other side and to contact, respectively, the LAA 2 on opposing sides of the LAA 2 adjacent the heart 1. The exclusion device 10 may be made from any suitable material such as stainless steel, tantalum, and, preferably, titanium, and alloys and combinations of any of the foregoing.

The exclusion device 10 preferably includes a hinge 16 that connects the second ends 12b, 14b. In preferred embodiments, hinge 16 is generally U-shaped and constitutes an integral extension of the second ends 12b, 14b of the first and second members 12, 14. However, the hinge 16 may comprise any technique for connecting the first and second members 12, 14 at their ends 12b, 14b in such a manner that permits the first ends 12, 14a of the exclusion device 10 to be moved in the first plane between an open position (shown, for example, in FIGS. 2, 4, and 7) and a closed position (shown, for example, in FIGS. 3, 5, and 6). In the open position, the first ends 12a, 14a are spaced from each other (see FIGS. 2and 4) such that the device 10 can be applied to the LAA 2 from the side rather than from the end. The hinge 16 preferably comprises a spring or is spring-tensioned so as to urge the first and second members 12, 14 away from each other.

In the preferred embodiments of the present invention, the first ends 12a, 14a of the first and second members 12, 14 interlock with each other to maintain the first and second members 12, 14 in the closed position—or, in other words, in a fixed position relative to each other. Preferably, the interlocking is accomplished by means of one or more teeth 15 located at end 14a, the teeth 15 interlocking with a blade 13 at end 12a. However, the exclusion device 10 may comprise any other suitable technique to maintain the exclusion device 10 in the closed position.

Figure 6:
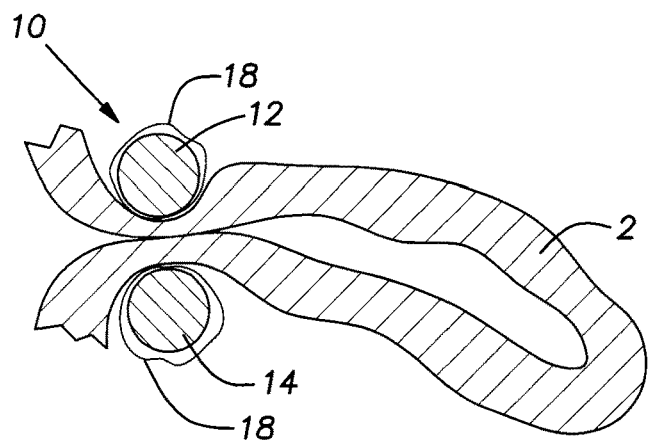
FIG. 6 is an enlarged sectional view taken along a plane indicated by line 6-6 in FIG. 5.
Figure 7:
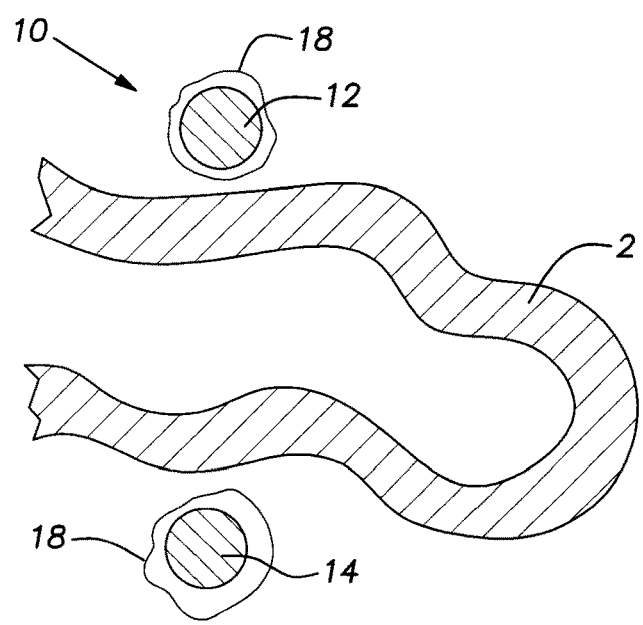
FIG. 7 shows the device of FIG. 6 in an open position.

In use, the first member 12 and second member 14 are placed in a closed position so as to dispose them generally parallel with each other and sufficiently close to each other to compress the LAA 2 between them and block the passage of thrombi therethrough without causing the development of necrotic tissue (see FIGS. 5 and 6). The portions of the first member 12 and second member 14 that contact the LAA 2 are configured to minimize stress concentrations in the LAA 2. In preferred embodiments of the present invention, the portions of the first member 12 and second member 14 that contact the LAA 2 are rounded. In some embodiments, the first and second members 12, 14 are substantially round in cross-section, as illustrated in FIGS. 4, 6, and 7, for example. In other embodiments, the cross-section of the first and second members 12, 14 are each rectangular with rounded ends, the longer dimension of the rectangle adapted to contact the LAA 2. In embodiments wherein end 14*a* comprises multiple teeth, the exclusion device may have multiple closed positions so as to adapt to various thicknesses of the walls of the LAA 2. This latter feature may also help to minimize stress concentrations in the LAA 2. It is important to note that the portion of the exclusion device 10 that clamps against the tissue is smooth and has no teeth that press against and traumatize the tissue.

In some embodiments of the present invention, a flexible cover 18 is provided to cover the substantial length of the first and second members 12, 14. The cover 18 does not extend beyond the first ends 12*a*, 14*a* of the first and second members 12, 14 such that the device 10, when provided with the flexible cover 18, remains open at the first ends 12*a*, 14*a* of the first and second members 12, 14 when the first and second members 12, 14 are in the first, open position. Also, the interlock connection between the first ends 12*a*, 14*a* of the first and second members 12, 14 is not covered. This permits the device 10 to be applied to the LAA 2 from the side rather than from the end. The cover 18 can be made of any material that is biocompatible with the LAA 2, but the preferred material is a polyester mesh. The cover 18, available preferably as variable density, tends to cushion the contact between the LAA 2 and the exclusion device 10 and assists in preventing undesired bleeding. An opening 20 in the exclusion device 10 may be provided for coupling the cover 18 to the exclusion device 10. For example, the cover 18 can be sewn to the exclusion device 10 via the opening 20. The cover 18 may also be further sewn to the heart 1 and/or LAA 2 at points 18*a* and 18*b*, for example.

Figure 8:
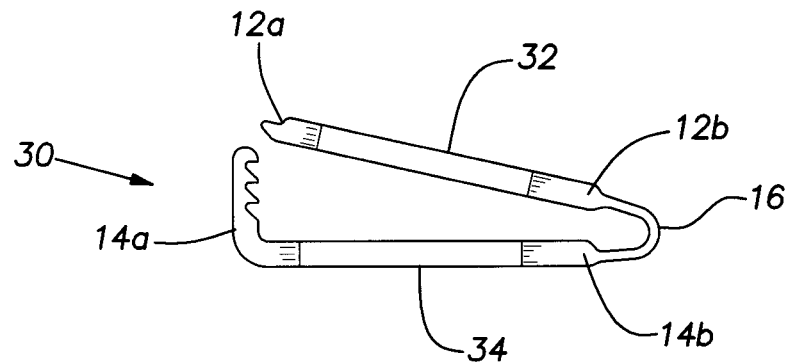
FIG. 8 is a side elevation view of an exclusion device in accordance with another embodiment of the present invention, the embodiment shown having arc-shaped first and second members.
Figure 9:
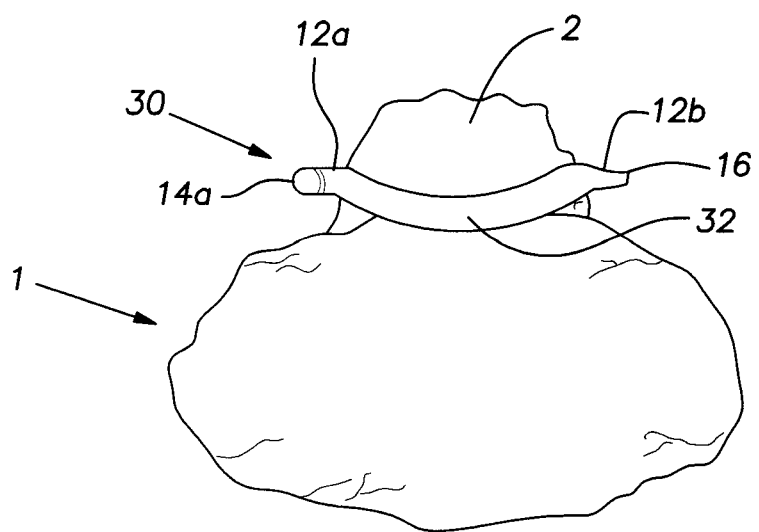
FIG. 9 is a top plan view of the device of FIG. 8 as used on a heart to exclude the LAA.

Referring now to FIGS. 8 and 9, show another embodiment of the present invention is indicated by the reference numeral 30. The embodiment 30 includes certain components identical or similar to those shown in the embodiment 10, and like reference numerals will be used where appropriate. In the embodiment 30, first and second members 32, 34 are comparable to first and second members 12, 14. However, the first member 32 and the second member 34 include central portions that are generally arc-shaped when viewed from above and lie in a second plane that is generally orthogonal to the first plane. First and second ends 12*a*, 12*b* are defined by straight segments that lie in the first plane and are disposed in a straight line relative to each other. The arc-shaped central portions lie out of the first plane. If desired, the cover 18 can be used with the embodiment 30.

As can be seen in FIG. 9, the shape of first and second members 32, 34 permits first and second members 32, 34 to be disposed toward or against the outer surface of the heart 1 while in use. The arc-shaped feature of the members 32, 34 therefore permits clamping of the LAA 2 to occur closer to the heart 1 while permitting hinging and locking to occur at a location somewhat away from the outer surface of the heart 1.

According to one method of the present invention for excluding the LAA 2, a first member 12 is provided, the member 12 being elongate and having first and second ends 12*a* and 12*b*. The first member 12 has a cross-section that minimizes stress concentrations in the LAA 2, the first member 12 being long enough to extend from one side of the LAA 2 to the other. The method also includes the step of providing a second member 14, the member 14 being elongate and having first and second ends 14*a* and 14*b*. The second member 14 has a cross-section that minimizes stress concentrations in the LAA 2, the second member 14 being long enough to extend from one side of the LAA 2 to the other.

The method also provides for disposing the first and second members 12, 14 on either side of the LAA 2 adjacent to the heart, the members 12, 14 being generally parallel with each other, and moving the first and second members 12, 14 sufficiently close to each other so as to compress the LAA 2 between the first and second members 12, 14 without causing the development of necrotic tissue. The method also includes maintaining the first and second members 12, 14 in a compressed position relative to the LAA 2.

The present invention also includes the step of providing a cover 18 as a flexible container for containing at least a portion of the first and second members 12, 14, the container being long enough to receive both the first and second members 12, 14 and being made of a material that is biocompatible with the LAA 2. The invention further includes the step of suturing the flexible container to the LAA 2. The invention also includes the step of providing the first and second members 12, 14 in an arc-shaped configuration so that clamping of the LAA can occur closer to the heart 1.

As will be apparent from the foregoing description, the exclusion device 10 according to the invention is relatively easy to manufacture and simple to use. The exclusion device 10 provides a convenient way to contain thrombi formed with the LAA of a patient, thereby significantly reducing the incidence of stroke in these patients. All of this is accomplished in a manner that minimizes stress concentrations in the LAA 2 and the accompanying formation of necrotic tissue. The device 10 further avoids punctures that could lead to difficult-to-control bleeding.

Although the invention has been described in its preferred form with a certain degree of particularity, it will be understood that the present disclosure of the preferred embodiments has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A method for excluding the left atrial appendage (LAA), comprising the steps of:
   providing a first, elongate member having first and second ends, the first member having a cross-section that will minimize stress concentrations in the LAA, the first member being long enough to extend from one side of the LAA to the other;
   providing a second, elongate member having first and second ends, the second member having a cross-section that will minimize stress concentrations in the LAA, the second member being long enough to extend from one side of the LAA to the other;
   disposing the first and second members on either side of the LAA adjacent the heart with the longitudinal axes of the first and second members generally parallel with each other;
   moving the first and second members sufficiently close to each other while maintaining the longitudinal axes generally parallel with each other to compress the LAA between the first and second members without causing the development of necrotic tissue:
maintaining the first and second members in a compressed position relative to the LAA;
providing a flexible container for the first and second members, the container being long enough to receive both the first and second members, the container being made of a material that is biocompatible with the LAA;
placing the first and second members in the container prior to the step of disposing the first and second members on either side of the LAA adjacent the heart with the longitudinal axes of the first and second members generally parallel with each other; and
suturing the flexible container to a selected one of the first member or the second member.

2. The method of claim 1, wherein the step of suturing the flexible container to a selected one of the first member or the second member is accomplished by forming an opening in the first member or the second member and sewing the cover to the opening.

3. The method of claim 1, wherein the flexible cover is a mesh made of polyester fabric.

4. The method of claim 1, wherein those portions of the first and second members that come in contact with the LAA are round in cross-section.

5. The method of claim 1, wherein the step of maintaining the first and second members in a compressed position relative to the LAA is accomplished by providing the first end of a selected one of the first or second members with a protrusion disposed approximately at a right angle to the member from which it extends, the protrusion having a tooth along its length and the first end of the other member being configured such that it can engage the tooth and thereby retain the first and second members in a fixed position relative to each other.

6. A method for excluding the left atrial appendage (LAA), comprising the steps of:
providing a first, elongate member having first and second ends, the first member having a cross-section that will minimize stress concentrations in the LAA, the first member being long enough to extend from one side of the LAA to the other;
providing a second, elongate member having first and second ends, the second member having a cross-section that will minimize stress concentrations in the LAA, the second member being long enough to extend from one side of the LAA to the other;
the first and second ends of the first and second members lying in a first plane;
providing a hinge that connects the second ends of the first and second members, the hinge being generally U-shaped and constituting an integral extension of the second ends of the first and second members to establish a structure that is closed at the second ends of the first and second members and open at the first ends of the first and second members when the first and second members are in a first, open position;
providing a flexible cover for the first and second members, the cover being biocompatible with the LAA and providing traction relative to the LAA;
wherein the cover does not extend beyond the first ends of the first and second members such that the device, when provided with the flexible cover, remains open at the first ends of the first and second members when the first and second members are in the first, open position;
disposing the first and second, elongate members on either side of the LAA;
moving the first ends of the first and second members in the first plane from the first, open position to a second, closed position in which the first and second members are disposed generally parallel with each other and being disposed sufficiently close to each other to compress the LAA between them without causing the development of damaged or necrotic tissue;
those portions of the first and second members that contact the LAA being configured to minimize stress concentrations in the LAA; and
maintaining the first and second members in a compressed position relative to the LAA.

7. The method of claim 6, further comprising the steps of:
forming an opening in a selected one of the first or second, elongate members; and
sewing the cover to the opening.

8. The method of claim 6, wherein the first and second members are made of a material selected from the group consisting of titanium, titanium alloys, stainless steel, tantalum, tantalum alloys, and mixtures thereof.

9. The method of claim 6, wherein the flexible cover is a mesh made of polyester fabric.

10. The method of claim 6, wherein those portions of the first and second members that come in contact with the LAA are round in cross-section.

11. The method of claim 6, wherein the step of maintaining the first and second members in a compressed position relative to the LAA is accomplished by providing the first end of a selected one of the first or second members with a protrusion disposed approximately at a right angle to the member from which it extends, the protrusion having a tooth along its length and the first end of the other member being configured such that it can engage the tooth and thereby retain the first and second members in a fixed position relative to each other.

12. The method of claim 11, wherein the protrusion has a plurality of teeth along its length and the first end of the other member being configured such that it can engage a selected tooth.

13. A method for excluding the left atrial appendage (LAA), comprising the steps of:
providing a first member having first and second ends adapted to extend from one side of the LAA to the other and to contact the LAA on a selected side thereof;
providing a second member having first and second ends adapted to extend from one side of the LAA to the other and to contact the LAA on the other side thereof;
the first and second ends of the first and second members lying in a first plane;
providing a hinge that connects the second ends of the first and second members, the hinge being generally U-shaped and constituting an integral extension of the second ends of the first and second members to establish a structure that is closed at the second ends of the first and second members and open at the first ends of the first and second members when the first and second members are in a first, open position;
the first and second members being generally arc-shaped when viewed from above and lying in a second plane that is generally orthogonal to the first plane;
providing a flexible cover for the first and second members, the cover being biocompatible with the LAA and providing traction relative to the LAA;
wherein the cover does not extend beyond the first ends of the first and second members such that the device, when provided with the flexible cover, remains open at the first ends of the first and second members when the first and second members are in the first, open position;

disposing the first and second, elongate members on either side of the LAA;

moving the first ends of the first and second members in the first plane from the first, open position to a second, closed position in which the first and second members are disposed generally parallel with each other and being disposed sufficiently close to each other to compress the LAA between them without causing the development of damaged or necrotic tissue;

those portions of the first and second members that contact the LAA being configured to minimize stress concentrations in the LAA; and maintaining the first and second members in a compressed position relative to the LAA.

14. The method of claim 13, wherein the first end of a selected one of the first or second members is defined by a protrusion disposed approximately at a right angle to the member from which it extends, the protrusion having a tooth along its length and the first end of the other member being configured such that it can engage the tooth and thereby retain the first and second members in a fixed position relative to each other.

15. The method of claim 14, wherein the protrusion has a plurality of teeth along its length and the first end of the other member being configured such that it can engage a selected tooth.

16. The method of claim 13, further comprising the steps of:

forming an opening in a selected one of the first or second, elongate members; and sewing the cover to the opening.

17. The method of claim 13, comprising the step of providing the first and second ends of the first and second members with straight segments that lie in the first plane.

18. The method of claim 13, wherein the first and second members are made of a material selected from the group consisting of titanium, titanium alloys, stainless steel, tantalum, tantalum alloys, and mixtures thereof.

19. The method of claim 13, wherein the flexible cover is a mesh made of polyester fabric.

20. The method of claim 13, wherein those portions of the first and second members that come in contact with the LAA are round in cross-section.

* * * * *